United States Patent [19]

Miyata

[11] Patent Number: 5,741,526

[45] Date of Patent: Apr. 21, 1998

[54] ANTIMICROBIAL AGENT

[75] Inventor: Shigeo Miyata, Kitakyushu, Japan

[73] Assignee: Kabushiki Kaisha Kaisui Kagaku Kenkyujo, Kitakyushu, Japan

[21] Appl. No.: 724,396

[22] Filed: Oct. 2, 1996

Related U.S. Application Data

[63] Continuation of Ser. No. 410,300, Mar. 24, 1995, abandoned.

[30] Foreign Application Priority Data

Mar. 25, 1994 [JP] Japan ................ 6-079714

[51] Int. Cl.$^6$ .................. A61K 33/34; C08K 3/22
[52] U.S. Cl. ............... 424/635; 424/633; 424/641; 524/431; 524/432; 524/433; 524/436
[58] Field of Search ............. 424/633, 635, 424/641; 524/431, 432, 433, 436

[56] References Cited

FOREIGN PATENT DOCUMENTS

| 0 448 566 | 8/1992 | European Pat. Off. ......... 424/641 |
| 0 536 879 | 4/1993 | European Pat. Off. ......... 252/609 |
| 0 544 502 | 6/1993 | European Pat. Off. ......... 562/84 |

*Primary Examiner*—James H. Reamer
*Attorney, Agent, or Firm*—Wenderoth, Lind & Ponack

[57] ABSTRACT

An antimicrobial agent containing at least one of an oxide solid solution of the formula (1),

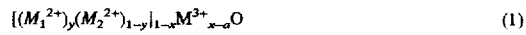

$$[(M_1^{2+})_y(M_2^{2+})_{1-y}]_{1-x}M^{3+}_{x-a}O \qquad (1)$$

wherein $M_1^{2+}$ is $Zn^{2+}$ and/or $Cu^{2+}$, $M_2^{2+}$ is $Mg^{2+}$ and/or $Ca^{2+}$, $M^{3+}$ is at least one trivalent metal selected from $Al^{3+}$, $Fe^{3+}$, $Co^{3+}$, $Cr^{3+}$, $In^{3+}$ and $Bi^{3+}$, x is a number in the range of $0.01 \leq x < 0.5$, y is a number in the range of $0 < y \leq 1$, and x−a shows that the number of $M^{3+}$ is decreased by a due to a lattice defect, and a hydrotalcite compound of the formula (2),

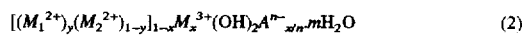

$$[(M_1^{2+})_y(M_2^{2+})_{1-y}]_{1-x}M_x^{3+}(OH)_2A^{n-}_{x/n} \cdot mH_2O \qquad (2)$$

wherein $M_1^{2+}$, $M_2^{2+}$ and $M^{3+}$ are as defined in the formula (1), $A^{n-}$ is an anion having a valence of n, x is as defined in the formula (1), y is a number in the range of $0 < y < 0.5$, and m is a number in the range of $0 \leq m \leq 2$, the above antimicrobial agent being free of, or almost free of, toxicity, excellent in heat resistance and weatherability, less expensive and excellent in dispersibility in resins, rubbers and fibers.

5 Claims, No Drawings

ANTIMICROBIAL AGENT

This application is a continuation of now abandoned application Ser. No. 08/410,300, filed Mar. 24, 1995.

FIELD OF THE INVENTION

The present invention relates to a novel antimicrobial agent of an oxide solid solution containing Zn and/or Cu as an active component, and an antimicrobial resin or rubber composition. More specifically, it relates to an antimicrobial agent which is free of, or almost free of, toxicity, is formed of fine particles having high heat resistance and weatherability and is excellent in dispersibility in resins, rubbers and coating compositions, specifically, an antimicrobial, antibacterial or antimold agent having these properties, and an antimicrobial resin or rubber composition containing the above antimicrobial agent.

PRIOR ART OF THE INVENTION

Microorganisms easily grow in warm and humid places, and bacteria and molds therefore easily grow in various places. For example, microorganisms sometimes occur in drinking water and foods to have some or great influences on human lives. Further, microorganism sometimes occur in or on foods, cosmetics, plastic products, wall paper, automotive interior and exterior fittings, construction materials, electric cables, other cables, synthetic leather, sealants, rubber hoses, adhesives, roofings, flooring materials, woods, coating compositions, and the like, to cause discolorations, offensive odors and degradations in strength. For example, microorganisms which occur on an electric cable may cause leakage of electricity and there is a risk of causing fire or an electrical shock. Further, microorganisms may damage precious cultural properties; molds which occur on a plastic may cause cancer; microorganisms may cause pneumonia; ticks or mites which live on bacteria may occur in large numbers; and ringworm may occur to cause tinea or scabies.

In recent years, there have been increasing demands for safe, clean and comfortable living environments by preventing the above sufferings from microorganisms, and various antimicrobial agents are commercially available. These antimicrobial agents are largely classified as follows.

Halides containing chlorine, bromine and iodine.

Inorganic compounds such as glass containing copper arsenite, cuprous oxide, silver nitrate, silver and copper.

Nitrogen-containing compounds such as amine and triazine.

Organic metal compounds containing metals such as arsenic, copper, mercury, tin and zinc.

Organic sulfur compounds such as isothiazolone, pyrithione and thiocyanic acid salt.

Phenol compounds such as chlorinated phenol, bisphenol and o-phenol.

Consumers are taking an increasing interest in safety, and this does not exclude consumers in the field of antimicrobial agents. For this reason, the use of a relatively highly safe inorganic antimicrobial agent containing supported silver is rapidly spreading. This inorganic antimicrobial agent is prepared by supporting silver on zeolite, apatite, silica or zirconium phosphate. However, this silver-containing inorganic antimicrobial agent is still toxic although it is less toxic than an organic antimicrobial agent. Further, the silver-containing inorganic antimicrobial agent has various defects in that it forms a color when it reacts with oxygen, that it foams when mixed with a resin and it is expensive due to the use of silver.

SUMMARY OF THE INVENTION

It is an object of the present invention to provide an antimicrobial agent which is free of, or almost free of, toxicity, is excellent in heat resistance and weatherability, is less expensive and is excellent in dispersibility in resins, rubbers and fibers, and an antimicrobial resin, rubber or fiber composition containing said antimicrobial agent.

According to the present invention, there is provided an antimicrobial agent containing, as an active ingredient, at least one of an oxide solid solution of the formula (1), $$[(M_1^{2+})_y(M_2^{2+})_{1-y}]_{1-x}M^{3+}_{x-a}O \quad (1)$$

wherein $M_1^{2+}$ is $Zn^{2+}$ and/or $Cu^{2+}$, $M_2^{2+}$ is $Mg^{2+}$ and/or $Ca^{2+}$, $M^{3+}$ is at least one trivalent metal selected from $Al^{3+}$, $Fe^{3+}$, $Co^{3+}$, $Cr^{3+}$, $In^{3+}$ and $Bi^{3+}$, x is a number in the range of $0.01 \leq x < 0.5$, preferably $0.1 \leq x \leq 0.4$, y is a number in the range of $0 < y \leq 1$, preferably $0.01 \leq y < 0.5$, and x−a shows that the number of $M^{3+}$ is decreased by a due to a lattice defect, and a hydrotalcite compound of the formula (2), $$[(M_1^{2+})_y(M_2^{2+})_{1-y}]_{1-x}M_x^{3+}(OH)_2 A^{n-}_{x/n} \cdot mH_2O \quad (2)$$

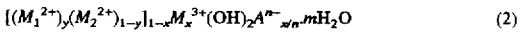

wherein $M_1^{2+}$, $M_2^{2+}$ and $M^{3+}$ are as defined in the formula (1), $A^{n-}$ is an anion having a valence of n, x is as defined in the formula (1), y is a number in the range of $0 < y < 0.5$, preferably $0.01 \leq y < 0.3$, and m is a number in the range of $0 \leq m \leq 2$.

Further, according to the present invention, there is provided an antimicrobial resin, rubber or fiber composition containing 100 parts by weight of a resin or rubber and 0.001 to 50 parts by weight, preferably 0.001 to 15 parts by weight, more preferably 0.01 to 5 parts by weight, of the above antimicrobial agent.

DETAILED DESCRIPTION OF THE INVENTION

The present inventors have made diligent studies to develop an antimicrobial agent which is free of toxicity, less expensive and excellent in heat resistance. As a result, it has been found that a solid solution in which ZnO and/or CuO is or are dissolved in MgO and/or CaO and further a trivalent metal ion such as $Al^{3+}$ is dissolved in the MgO and/or CuO remarkably shows excellent antimicrobial activity over any one of ZnO, CuO and a combination of ZnO and CuO. It has been already known that free Zn ion and Cu ion from ZnO and CuO exhibit antimicrobial activity like Ag ion. However, the activity of Zn ion and Cu ion is lower than that of Ag ion, whereas it has been found that an oxide which is a solid solution produced by dissolving a ZnO and/or CuO in MgO and/or CaO and further dissolving a trivalent metal ion such as $Al^{3+}$ in the MgO and/or CaO shows remarkably improved antimicrobial activity. It has bee also found that a hydrotalcite which is a solid solution prepared by dissolving $Zn(OH)_2$ and/or $Cu(OH)_2$ in $Mg(OH)_2$ and/or $Ca(OH)_2$ and further dissolving a trivalent metal ion such as $Al^{3+}$ in the $Mg(OH)_2$ and/or $Ca(OH)_2$ shows remarkably improved antimicrobial activity.

The antimicrobial agent of the present invention is less expensive than a conventional inorganic antimicrobial agent containing supported silver. Further, the antimicrobial agent of the present invention is excellent in heat resistance so that it is free of the problem of foaming at a temperature at which a resin or a rubber is processed. Moreover, the antimicrobial agent of the present invention, which is a ZnO-based and/or $Zn(OH)_2$-based solid solution is naturally less toxic than an organic antimicrobial agent, and it is also less toxic than an inorganic antimicrobial agent containing supported silver. It is one of limited numbers of compounds safe to human bodies.

An oxide and hydroxide of Zn and Cu work as a decomposing agent when incorporated into polyvinyl chloride, whereas the antimicrobial agent of the present invention contains MgO and/or CaO, or Mg(OH)$_2$ and/or Ca(OH)$_2$, and therefore, the antimicrobial of the present invention is advantageous in that MgO and/or CaO, or Mg(OH)$_2$ and/or Ca(OH)$_2$ work(s) as a stabilizer for polyvinyl chloride so that these mask the decomposing activity of the oxide and hydroxide of Zn and Cu. Further, a solid solution containing ZnO and Zn(OH)$_2$ is white in color, and is free of the problem of discoloring caused by silver.

The compound of the formula (1) and the compound of the formula (2), provided by the present invention, are solid solutions of oxides or hydroxides of divalent metals ($M_1^{2+}$, $M_2^{2+}$) and trivalent metal oxide or hydroxide and the divalent metal oxides or hydroxides are main components. Therefore, diffraction pattern of the solid solution by powder X-ray diffraction has the following characteristics. The compounds of the present invention show diffraction patterns of the divalent metal oxides or hydroxides, while they show no diffraction pattern of the trivalent metal oxide or hydroxide, since the trivalent metal oxide or hydroxide and the divalent metal oxides or hydroxides form a solid solution in which the trivalent metal oxide or hydroxide is dissolved in the divalent metal oxides or hydroxides. When the calcination temperature is high (e.g., about 900° C. or higher), however, they show a weak diffraction pattern of a byproduct having a spinel structure ($M_1^{2+}$ or $M_2^{2+}$)$M^{3+}_2O_4$.

In the compound of the formula (1), as x increases, $M_1^{2+}$ forms a finer crystallite, and the antimicrobial activity of the compound improves. However, when x is 0.5 or greater, the amount of by-produced spinel-structure compounds increases, and the antimicrobial activity tends to decrease. It is assumed that $M_2^{2+}$ is dissolved in $M_1^{2+}$, or $M_1^{2+}$ is dissolved in $M_2^{2+}$, and that these mutually inhibit their crystal growth and form a crystallite, and as a result, improve the antimicrobial activity. When a solid solution containing a trivalent metal ion such as $Al^{3+}$ is formed, the solid solution forms a fine oxide having a large specific area, and $Zn^{2+}$ and/or $Cu^{2+}$ are more easily released and eluted into water. In the compound of the formula (2), when x exceeds 0.4, the amount of $M^{3+}$ exceeds the limit of the amount in which all of $M^{3+}$ can form a solid solution, and a hydroxide of $M^{3+}$ may be formed as a byproduct. As a result, the compound of the formula (2) tends to show a decreased antimicrobial activity. This tendency can be conspicuously observed when x exceeds 0.5. When x is 0.4 or less, the compound of the formula (2) can be obtained as a fine crystallite, and can exhibit high antimicrobial activity. Mg(OH)$_2$ and Ca(OH)$_2$ are essential components for the exhibition of antimicrobial activity and the improvement of heat resistance. When y is 0.5 or more, the decomposition of the compound of the formula (1) by dehydration starts at about 150° C.

The compound of the formula (1) can be produced by calcining the hydrotalcite compound of the formula (2'),

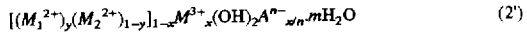
(2')

wherein $M_1^{2+}$, $M_2^{2+}$ and $M^{3+}$ are as defined in the formula (1), $A^{n-}$ is an anion having a valence of n, x is as defined in the formula (1), y is a number in the range of $0<y\leq 1$ and m is a number in the range of $0\leq m\leq 2$, at a temperature of 2,000° C. or lower, preferably 1,500° C. or lower, more preferably between approximately 300° and 1,300° C., particularly preferably between approximately 400° and 1,000° C., for approximately 0.1 to 10 hours. The calcined powder can be used as it is. For incorporating the calcined powder into a resin or a rubber, it may be surface-treated with a conventional surface treating agent for improving it in dispersibility. The surface treating agent includes higher fatty acids, alkali metal or alkaline earth metal salts of higher fatty acids, phosphate esters, silane-, titanate- or aluminum-containing coupling agents, and esters of polyhydric alcohols and higher fatty acids.

Specific examples of the above surface treating agent preferably include higher fatty acids having at least 10 carbon atoms such as stearic acid, erucic acid, palmitic acid, lauric acid and behenic acid; sulfuric acid esters of higher alcohols such as stearyl alcohol and oleyl alcohol; anionic surfactants such as ester-bond sulfuric acid ester, ester-bond sulfonate, amide-bond sulfonic acid salt, ether-bond sulfonic acid salt, ether-bond alkylallylsulfonic acid salt, ester-bond alkylallylsulfonic acid salt and amide-bond alkylallylsulfonic acid salt; phosphate esters such as mono- or diester of orthophosphoric acid and oleyl alcohol or stearyl alcohol and a mixture of these mono- and diesters which are acid type, alkali type or amine salts; silane-coupling agents such as vinylethoxysilane, vinyl-tris(2-methoxy-ethoxy)silane, gamma-methacryloxypropyltrimethoxy-silane, gamma-aminopropyltrimethoxysilane, beta-(3,4-epoxycyclohexyl)ethyltrimethoxysilane, gamma-glydidoxypropyltrimethoxysilane and gamma-mercaptopropyltrimethoxysilane; titanate-containing coupling agents such as isopropyltriisostearoyl titanate, isopropyltris(dioctylpyrophosphate) titanate, isopropyltri (N-aminoethyl-aminoethyl) titanate and isopropyltridecylbenzenesulfonyl titanate; aluminum-containing coupling agents such as acetoalkoxyaluminum diisopropylate; and esters of polyhydric alcohol and fatty acid such as glycerin monostearate and glycerin monooleate.

The compounds of the formulae (1) and (2) can be surface-treated (surface-coated) by a known method such as a dry method or a wet method. For example, the surface treatment of the compound of the formula (2) by a wet method can be carried out by adding a water-soluble surface treating agent to a slurry of the compound of the formula (2) with stirring. The surface treatment of the compound of the formula (1) by a dry method can be carried out by adding the surface treating agent in the state of a liquid, an emulsion or a solid to a powder of the compound of the formula (1) while the powder is fully stirred with a Henschel mixer, and fully mixing these under heat or no heat. The amount of the surface treating agent may be selected as required, while this amount is preferably about 0.1 to about 10% by weight based on the weight of the compound of the formula (1) or (2).

The surface-treated compound of the formula (1) or (2) may be treated by granulation, drying, milling, classification, etc, as required, to bring it into the state of a final product.

The antimicrobial agent of the present invention is used in various fields where microorganisms may have bad influences, such as the fields of drinking water, foods, resins, rubbers, wall paper, interior materials for a bath room, cement, sanitary earthenware, writing tools, underwear, electric cables, flooring materials, shower curtains, foamed urethane, buoy ropes, vinyl sheets, films for agricultures, synthetic leathers, electric appliances and parts therefor, waxes, fats and oils, cutting oils, dishes, tableware, bathtubs, adhesives, packaging materials, sheds for keeping animals, sealants, construction materials, furniture, fiber articles such as cloth, tents, socks and unwoven fabrics, antifouling agents (ship bottom paints), coating compositions, adhesives, woods, bamboo works, cosmetics, swimming pools, cooling towers and chemicals typified by substitutes for copper agents such as lime Bordeaux liquid as a sterilizer for agriculture.

When the antimicrobial agent of the present invention is incorporated into a resin, a rubber or a fiber, the amount of the antimicrobial agent per 100 parts by weight of the resin, the rubber or the fiber is generally 0.001 to 50 parts by weight, preferably 0.01 to 10 parts by weight, more preferably 0.1 to 5 parts by weight, while the antimicrobial agent of the present invention may be incorporated in a proper amount as required depending upon use.

The antimicrobial agent of the present invention may have a secondary particle diameter of approximately 0.1 to 1 μm. Further, the hydroxide of the formula (2) is stable at least up to a processing temperature of about 300° C., and the oxide of the formula (1) is stable at least up to a processing temperature of about 1,300° C. Further, the oxide of the formula (1) and the hydroxide of the formula (2) are also stable to ultraviolet light and radiation. For example, the antimicrobial agent of the present invention may be mixed with a spinning solution, melted and kneaded before spinning. As a result, the antimicrobial agent of the present invention can overcome the defect of a prior art antimicrobial agent which gradually loses its effect when washed. Sanitary earthenware or earthenware for tableware are finished by firing the glazed earthenware at 1,200° C. or a little higher, and when the antimicrobial agent of the present invention is fired at such a high temperature, it retains the antimicrobial activity. Further, the antimicrobial agent of the present invention is free from foaming a molded article by evaporating water at a temperature at which a resin and a rubber are processed, and it is excellent in dispersibility in a resin, a rubber and a fiber and almost free from decreasing the mechanical strength of a molded article. As a result, the molded article can have an excellent appearance. The antimicrobial agent of the present invention can work as a heat stabilizer for resins such as polyvinyl chloride, and can overcome the problem of the oxides and hydroxides of Cu and Zn decomposing a polyvinyl chloride.

Although not specially limited, the resin, the rubber and the fiber used in the present invention include thermoplastic resins such as polyethylene, a copolymer of ethylene and other α-olefin, a copolymer of ethylene and any one of vinyl acetate, ethyl acrylate and methyl acrylate, polypropylene, a copolymer of propylene and other α-olefin, polybutene-1, polystyrene, a copolymer of styrene and acrylonitrile or butadiene, a copolymer of ethylene and propylenediene rubber or butadiene, vinyl acetate, polyacrylate, polymethacrylate, polyurethane, polyester, polyether, polyamide, polyvinyl chloride, a copolymer of vinyl chloride and vinyl acetate, polyvinylidene chloride, polyphenylene oxide and polycarbonate, thermosetting resins such as a phenolic resin, a melamine resin, an epoxy resin, an unsaturated polyester resin and an alkyd resin; rubbers such as EPDM, SBR, NBR, butyl rubber, isoprene rubber and chlorosulfonated polyethylene; and fibers such as acrylic fiber, acetate fiber, nylon, pulp, vinylidene chloride fiber, vinylon, non-woven fabrics, polyacetal fiber, polyurethane fiber, polyester fiber, polyethylene fiber and polypropylene fiber.

The present invention will be explained more in detail hereinafter with reference to Examples, in which "%" and "part" stand for "% by weight" and "part by weight" unless otherwise specified.

EXAMPLE 1

A zinc nitrate/aluminum nitrate mixed aqueous solution in an amount of 2 liters ($Zn^{2+}$=0.7 mol/l, $Al^{3+}$=0.3 mol/l) was added to a mixture of 2 liters of a sodium hydroxide aqueous solution containing 2 mol/l of sodium hydroxide with 0.5 liter of a sodium carbonate aqueous solution containing 0.6 ml/l of sodium carbonate with stirring over about 2 minutes, and the mixture was allowed to react at a temperature of about 30° C. The resultant reaction mixture in the form of a slurry was filtered under reduced pressure, washed with water and dried. The resultant dry product was milled to form a powder, and the powder was placed in a siliconitt furnace and calcined at 400° C. for 1 hour. The calcined powder was measured for a chemical composition by a chelate titration method, its crystal structure was identified by power X-ray diffractometry, and it was also measured for a BET specific surface area by a nitrogen adsorption method. Further, the calcined powder was evaluated for antimicrobial activity as follows. A solution of microorganisms was applied to flat plates of an agar medium and the microorganisms were cultured. Antimicrobial solutions containing predetermined concentrations of the calcined powder (antimicrobial agent) was added to the plates, and a minimum concentration at which the growth of the microorganisms was inhibited was taken as a minimum growth inhibition concentration. The lower the minimum growth inhibition concentration is, the higher the antimicrobial activity is. The diffraction pattern of the calcined powder slightly shifted toward a higher angle side, while it was the diffraction pattern of ZnO alone. It is therefore seen hat the calcined powder was a solid solution of $Al_2O_3$ in ZnO. Table 1 shows the results of the above evaluations. The calcined powder had the following chemical composition.

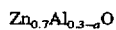

$Zn_{0.7}Al_{0.3-a}O$

EXAMPLE 2

A zinc chloride/magnesium chloride/aluminum chloride mixed solution in an amount of 4 liters ($Zn^{2+}$=0.1 mol/l, $Mg^{2+}$=0.6 mol/l, $Al_{3+}$=0.3 mol/l) was poured into an over-flowable reaction vessel having a volume of 2 liters at a rate of about 50 ml/minutes with a quantitative pump with stirring, and at the same time, 4 liters of a sodium hydroxide aqueous solution containing 2 mol/l of sodium hydroxide was poured into the over-flowable reaction vessel at a rate of about 35 ml/minute with a quantitative pump with stirring. During the above procedures, the mixture was maintained at a pH of about 9.0 at a temperature of about 30° C. The resultant reaction mixture in the form of a slurry was filtered under reduced pressure, washed with 5 liters of a sodium carbonate aqueous solution containing 0.2 mol/l of sodium carbonate, further washed with water, dried and milled. The resultant powder was calcined in a siliconitt furnace at 500° C. for 1 hour. The calcined powder showed an X-ray diffraction pattern of MgO alone, which shows that the calcined powder was a solid solution of both ZnO and $Al_2O_3$ in MgO. The calcined powder was evaluated in the same manner as in Example 1. Table 1 shows the results. The calcined powder had the following chemical composition.

$Zn_{0.1}Mg_{0.6}Al_{0.3-a}O$

EXAMPLE 3

A calcined powder was prepared in the same manner as in Example 1 except that 2 liters of the zinc nitrate/aluminum nitrate mixed aqueous solution was replaced with 2 liters of a copper nitrate/aluminum nitrate mixed aqueous solution ($Cu^{2+}$=0.8 mol/l, $Al_{3+}$=0.2 mol/l). The calcined powder showed an X-ray diffraction pattern which slightly shifted to a high angle side, while it was a diffraction pattern of CuO alone. It was therefore found to be a solid solution of $Al_2O_3$ in CuO. The calcined powder was evaluated in the same manner as in Example 1. Table 1 shows the results. The calcined powder had the following chemical composition.

$$Cu_{0.8}Al_{0.2-a}O$$

EXAMPLE 4

A calcined powder was prepared in the same manner as in Example 1 except that 2 liters of the zinc nitrate/aluminum nitrate mixed aqueous solution was replaced with 2 liters of a copper nitrate/magnesium nitrate/aluminum nitrate mixed aqueous solution ($Cu^{2+}$=0.1 mol/l, $Mg^{2+}$=0.65 mol/l, $Al^{3+}$=0.25 mol/l). The calcined powder showed an X-ray diffraction pattern of MgO alone. It is therefore seen that the calcined powder was a solid solution of CuO and $Al_2O_3$ in MgO. The calcined powder was evaluated in the same manner as in Example 1. Table 1 shows the results. The calcined powder had the following chemical composition.

$$Cu_{0.1}Mg_{0.65}Al_{0.25-a}O$$

EXAMPLE 5

A copper nitrate/calcium nitrate/aluminum nitrate mixed aqueous solution in an amount of 2 liters ($Cu^{2+}$=0.5 mol/l, $Ca^{2+}$=0.1 mol, $Al^{3+}$=0.4 ml/l) was added to 2 liters of a sodium hydroxide aqueous solution containing 2 mol/l of sodium hydroxide with stirring and the mixture was allowed to react at 27° C. The resultant reaction mixture in the form of a slurry was filtered under reduced pressure, washed with water, dried and milled. The resultant powder was calcined in a siliconitt furnace at 600° C. for 1 hour. The calcined powder showed an X-ray diffraction pattern of CuO and a small amount of $CuAl_2O_4$. The calcined powder was evaluated in the same manner as in Example 1. Table 1 shows the results. The calcined powder had the following chemical composition.

$$Cu_{0.5}Ca_{0.1}Al_{0.4-a}O$$

EXAMPLE 6

A copper sulfate/zinc sulfate/magnesium sulfate/aluminum sulfate mixed solution in an amount of 2 liters ($Cu^{2+}$=0.2 mol/l, $Zn^{2+}$=0.1 mol/l, $Mg^{2+}$=0.4 mol/l, $Al^{3+}$=0.3 mol/l) was added to 2 liters of a sodium hydroxide aqueous solution containing 2 mol/l of sodium hydroxide with stirring and the mixture was allowed to react at 30° C. The resultant reaction mixture in the form of a slurry was filtered under reduced pressure, washed with 3 liters of a sodium carbonate aqueous solution containing 0.2 mol/l of sodium carbonate, further washed with water, dried and milled. The resultant powder was calcined in a siliconit furnace at 500° C. for 1 hour. The calcined powder showed an X-ray diffraction pattern of MgO alone. It is therefore seen that the calcined powder was a solid solution of CuO, ZnO and $Al_2O_3$ in MgO. The calcined powder was evaluated in the same manner as in Example 1. Table 1 shows the results. The calcined powder had the following chemical composition.

$$Cu_{0.2}Zn_{0.1}Mg_{0.4}Al_{0.3-a}O$$

EXAMPLE 7

The milled powder obtained in Example 2, which was not calcined, was measured for an X-ray diffraction pattern to show substantially the same X-ray diffraction pattern as that of hydrotalcites. The above powder was also measured for a BET specific surface area, and evaluated for antimicrobial activity. Table 1 shows the results. The above powder (not calcined) had the following chemical composition.

$$Zn_{0.1}Mg_{0.6}Al_{0.3}(OH)_2(CO_3)_{0.15} \cdot 0.55H_2O$$

EXAMPLE 8

The milled powder obtained in Example 4, which was not calcined, was measured for an X-ray diffraction pattern to show substantially the same X-ray diffraction pattern as that of hydrotalcites. The above powder was also measured for a BET specific surface area, and evaluated for antimicrobial activity. Table 1 shows the results. The above powder (not calcined) had the following chemical composition.

$$Cu_{0.1}Mg_{0.65}Al_{0.25}(OH)_2(CO_3)_{0.125} \cdot 0.625H_2O$$

EXAMPLE 9

The dry powder obtained in Example 2, which was not calcined, was calcined at 1,200° C. for 1 hour. The calcined powder showed X-ray diffraction patterns of MgO and $(MgZn)Al_2O_4$. The diffraction pattern of MgO shifted to a low angle side to some extent, which shows that ZnO was dissolved. The calcined powder was evaluated in the same manner as in Example 1. Table 1 shows the results. The calcined powder had the following chemical composition.

$$Zn_{0.1}Mg_{0.6}Al_{0.3-a}O$$

COMPARATIVE EXAMPLES 1–3

Cupric oxide as a first grade reagent (Comparative Example 1), zinc oxide (Comparative Example 2) and a commercially available, copper-supporting borosilicate glass (Comparative Example 3) were evaluated for antimicrobial activities. Table 1 shows the results.

TABLE 1

| | BET specific surface area $m^2/g$ | Antimicrobial activity | |
|---|---|---|---|
| | | *Escherichia coli* | *Staphylococcus aureus* |
| Ex. 1 | 210 | 0.15 | 0.05 |
| Ex. 2 | 275 | 0.10 | 0.05 |
| Ex. 3 | 184 | 0.05 | 0.025 |
| Ex. 4 | 305 | 0.025 | 0.01 |
| Ex. 5 | 276 | 0.025 | 0.025 |
| Ex. 6 | 280 | 0.0125 | 0.0125 |
| Ex. 7 | 104 | 0.8 | 0.4 |
| Ex. 8 | 118 | 0.8 | 0.2 |
| Ex. 9 | 13 | 0.2 | 0.1 |
| CEx. 1 | 6 | above 1.0 | above 1.0 |
| CEx. 2 | 7 | above 1.0 | above 1.0 |
| CEx. 3 | — | 1.0 | 0.5 |

Note: Ex. = Example, CEx. = Comparative Example CEx. 1; CuO, CEx. 2; ZnO, CEx. 3; copper-supporting borosilicate glass Examples 10 and 11, and Comparative Examples 4 and 5

| | |
|---|---|
| Polyvinyl chloride (average polymerization degree 1,300) | 100 parts |
| Dioctyl phthalate | 50 parts |
| Ca/Zn-based complex stabilizer | 2 parts |
| Antimicrobial agent | 2 parts |

The above components were uniformly mixed, and the mixture was melt-kneaded with a roll at 170° C. for 3 minutes. The resultant composition was molded into a sheet having a thickness of about 1 mm under a pressure of 200 kg/cm² at 170° C. for 2 minutes with a press molding machine. Penicillium was sprinkled over the sheet, and was observed for its growth state thereafter. Table 2 shows the results. Example 7 used the antimicrobial agent obtained in Example 1, Example 8 used the antimicrobial agent obtained in Example 5, Comparative Example used CuO of Comparative Example 1, and Comparative Example 5 used ZnO of Comparative Example 2.

TABLE 2

|  | Antimicrobial Activity (days for culturing) | | | |
| --- | --- | --- | --- | --- |
|  | 7 | 14 | 21 | 28 |
| Ex. 10 | 0 | 0 | 0 | 1 |
| Ex. 11 | 0 | 0 | 0 | 0 |
| CEx. 4 | 2 | 3 | 3 | 4 |
| CEx. 5 | 3 | 4 | 4 | 4 |

Evaluation ratings:
0 = No growth of mold
1 = Slight growth of mold
2 = A little growth of mold
3 = Ordinary growth of mold
4 = Vigorous growth of mold As explained above, the present invention provides an antimicrobial agent of an oxide solid solution and/or a hydrotalcite compound containing copper and/or zinc as an active component. The antimicrobial agent of the present invention is a powder which is free of, or almost free of, toxicity and is excellent in heat resistance and weatherability. Further, the antimicrobial of the present invention has high dispersibility in resins, rubbers, fibers and coating compositions, and yet, it does not impair the strength of resins, and the like, nor does it impair the appearance of articles formed of resins, and the like.

What is claimed is:

1. An antimicrobial agent containing, as an active ingredient, at least one of an oxide solid solution of the formula (1),

  (1)

wherein $M_1^{2+}$ is $Zn^{2+}$ and/or $Cu^{2+}$, $M_2^{2+}$ is $Mg^{2+}$ and/or $Ca^{2+}$, $M^{3+}$ is at least one trivalent metal selected from $Al^{3+}$, $Fe^{3+}$, $Co^{3+}$, $Cr^{3+}$, $In^{3+}$ and $Bi^{3+}$, x is a number in the range of $0.01 \leq x < 0.5$, y is a number in the range of $0 < y \leq 1$, and x–a shows that the number of $M^{3+}$ is decreased by a due to a lattice defect.

2. An antimicrobial agent according to claim 1, wherein the oxide solid solution of the formula (1) is a solid solution produced by calcining a hydrotalcite compound of the formula (2'),

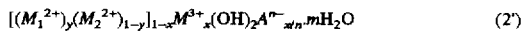  (2')

wherein $M_1^{2+}$, $M_2^{2+}$ and $M^{3+}$ are as defined in the formula (1), $A^{n-}$ is an anion having a valence of n, x is as defined in the formula (1), y is a number in the range of $0 < y \leq 1$ and m is a number in the range of $0 \leq m \leq 2$, at a temperature of 2,000° C. or lower.

3. An antimicrobial agent according to claim 1, wherein the compound of the formula (1) is surface treated with at least one surface treating agent selected from the group consisting of higher fatty acids, alkali metal salts of higher fatty acids, anionic surfactants, phosphate esters of higher alcohols, silane-containing coupling agents, titanate-containing coupling agents, or aluminum-containing coupling agents, and esters of polyhydric alcohols and higher fatty acids.

4. An antimicrobial agent according to claim 1, wherein, in the solid solution of the formula (1), $M_1^{2+}$ is $Zn^{2+}$ and/or $Cu^{2+}$, $M_2^{2+}$ is $Mg^{2+}$ and/or $Ca^{2+}$, and $M_3^{3+}$ is $Al^{3+}$.

5. An antimicrobial resin, rubber or fiber composition containing 100 parts by weight of a resin, a rubber or a fiber and 0.001 to 50 parts by weight of the antimicrobial agent as recited in claim 1.

* * * * *